(12) United States Patent
Mazzone

(10) Patent No.: US 11,213,423 B2
(45) Date of Patent: Jan. 4, 2022

(54) PROXIMAL MOUNTING OF TEMPERATURE SENSOR IN INTRAVASCULAR TEMPERATURE MANAGEMENT CATHETER

(71) Applicant: Zoll Circulation, Inc., San Jose, CA (US)

(72) Inventor: James Mazzone, San Jose, CA (US)

(73) Assignee: Zoll Circulation, Inc., San Jose, CA (US)

( * ) Notice: Subject to any disclaimer, the term of this patent is extended or adjusted under 35 U.S.C. 154(b) by 778 days.

(21) Appl. No.: 14/675,452

(22) Filed: Mar. 31, 2015

(65) Prior Publication Data

US 2016/0287433 A1 Oct. 6, 2016

(51) Int. Cl.
*A61F 7/12* (2006.01)
*A61F 7/00* (2006.01)

(52) U.S. Cl.
CPC ........ *A61F 7/12* (2013.01); *A61F 2007/0054* (2013.01); *A61F 2007/0056* (2013.01);
(Continued)

(58) Field of Classification Search
CPC .................................. G01K 7/16; G01K 7/22
See application file for complete search history.

(56) References Cited

U.S. PATENT DOCUMENTS 1,459,112 A 6/1923 Mehl
1,726,761 A 9/1929 Palmer
(Continued)

FOREIGN PATENT DOCUMENTS

DE 19531935 2/1997
EP 0663529 B1 5/1997
(Continued)

OTHER PUBLICATIONS

Jeremy Thomas Dabrowiak, "Heat Exchange System for Patient Temperature Control with Multiple Coolant Chambers for Multiple Heat Exchange Modalities", related pending U.S. Appl. No. 14/175,545 non-final office action dated Feb. 12, 2016.
(Continued)

*Primary Examiner* — Kaitlyn E Smith
(74) *Attorney, Agent, or Firm* — Fish & Richardson P.C.

(57) ABSTRACT

An intravascular temperature management catheter includes a shaft through which working fluid can circulate to and from a proximal location on the shaft. The catheter extends from a connector hub. At least one heat exchange member is supported by a distal part of the shaft or other part of the catheter to receive circulating working fluid from the proximal location. A temperature sensor is supported on the catheter for generating a temperature signal representative of blood temperature to a control system. The temperature sensor includes first and second conductive leads having respective first and second distal segments on or in the catheter shaft. The first and second distal segments are arranged to be in thermal contact with blood flowing past the catheter when the catheter is disposed in a blood vessel of a patient. Also, the temperature sensor includes a joining body connected to proximal segments of the first and second leads. The joining body may be supported in the hub or in another location proximal to the first and second conductive leads.

21 Claims, 2 Drawing Sheets

(52) U.S. Cl.
CPC ............... *A61F 2007/0086* (2013.01); *A61F 2007/0093* (2013.01); *A61F 2007/0095* (2013.01); *A61F 2007/0096* (2013.01); *A61F 2007/126* (2013.01)

(56) References Cited

U.S. PATENT DOCUMENTS

| | | | |
|---|---|---|---|
| 1,857,031 | A | 5/1932 | Schaffer |
| 2,663,030 | A | 12/1953 | Dahiberg |
| 2,673,987 | A | 4/1954 | Upshaw et al. |
| 3,225,191 | A | 12/1965 | Calhoun |
| 3,369,549 | A | 2/1968 | Armao |
| 3,425,419 | A | 2/1969 | Dato |
| 3,504,674 | A | 4/1970 | Swenson et al. |
| 3,726,269 | A | 4/1973 | Webster, Jr. |
| 3,744,565 | A | 7/1973 | Fletcher |
| 3,751,077 | A | 8/1973 | Hiszpanski |
| 3,937,224 | A | 2/1976 | Uecker |
| 3,945,063 | A | 3/1976 | Matsuura |
| 4,038,519 | A | 7/1977 | Foucras |
| 4,065,264 | A | 12/1977 | Lewin |
| 4,103,511 | A | 8/1978 | Kress et al. |
| 4,126,132 | A | 11/1978 | Portner et al. |
| 4,153,048 | A | 5/1979 | Magrini |
| 4,173,228 | A | 11/1979 | Van Steenwyk et al. |
| 4,181,132 | A | 1/1980 | Parks |
| 4,298,006 | A | 11/1981 | Parks |
| 4,459,468 | A | 7/1984 | Bailey |
| 4,532,414 | A | 7/1985 | Shah et al. |
| 4,554,793 | A | 11/1985 | Harding, Jr. |
| 4,581,017 | A | 4/1986 | Sahota |
| 4,638,436 | A | 1/1987 | Badger et al. |
| 4,653,987 | A | 3/1987 | Tsuji et al. |
| 4,661,094 | A | 4/1987 | Simpson |
| 4,665,391 | A | 5/1987 | Spani |
| 4,672,962 | A | 6/1987 | Hershenson |
| 4,754,752 | A | 7/1988 | Ginsburg et al. |
| 4,787,388 | A | 11/1988 | Hofmann |
| 4,813,855 | A | 3/1989 | Leveen et al. |
| 4,849,196 | A | 7/1989 | Yamada et al. |
| 4,852,567 | A | 8/1989 | Sinofsky |
| 4,860,744 | A | 8/1989 | Johnson et al. |
| 4,906,237 | A | 3/1990 | Johansson et al. |
| 4,941,475 | A | 7/1990 | Williams et al. |
| 5,092,841 | A | 3/1992 | Spears |
| 5,103,360 | A | 4/1992 | Maeda |
| 5,106,360 | A | 4/1992 | Ishiwara et al. |
| 5,174,285 | A | 12/1992 | Fontenot |
| 5,192,274 | A | 3/1993 | Bierman |
| 5,195,965 | A | 3/1993 | Shantha |
| 5,211,631 | A | 5/1993 | Sheaff |
| 5,269,758 | A | 12/1993 | Taheri |
| 5,281,215 | A | 1/1994 | Milder |
| 5,304,214 | A | 4/1994 | DeFord et al. |
| 5,342,301 | A | 8/1994 | Saab |
| 5,344,436 | A | 9/1994 | Fontenot et al. |
| 5,370,675 | A | 12/1994 | Edwards et al. |
| 5,383,856 | A | 1/1995 | Bersin |
| 5,403,281 | A | 4/1995 | O'Neill et al. |
| 5,433,740 | A | 7/1995 | Yamaguchi |
| 5,437,673 | A | 8/1995 | Baust et al. |
| 5,458,639 | A | 10/1995 | Tsukashima et al. |
| 5,486,207 | A | 1/1996 | Mahawili |
| 5,486,208 | A | 1/1996 | Ginsburg |
| 5,507,792 | A | 4/1996 | Mason et al. |
| 5,531,714 | A | 7/1996 | Dahn et al. |
| 5,531,776 | A | 7/1996 | Ward et al. |
| 5,596,995 | A | 1/1997 | Sherman et al. |
| 5,624,392 | A | 4/1997 | Saab |
| 5,634,907 | A | 6/1997 | Rani et al. |
| 5,676,670 | A | 10/1997 | Kim |
| 5,686,658 | A * | 11/1997 | Boren ............... G01M 3/3245 73/314 |
| 5,701,905 | A | 12/1997 | Esch |
| 5,709,564 | A | 1/1998 | Yamada et al. |
| 5,709,654 | A | 1/1998 | Klatz et al. |
| 5,716,386 | A | 2/1998 | Ward et al. |
| 5,730,720 | A | 3/1998 | Sites et al. |
| 5,733,319 | A | 3/1998 | Neilson et al. |
| 5,737,782 | A | 4/1998 | Matsuura et al. |
| 5,759,017 | A | 6/1998 | Patton et al. |
| 5,776,079 | A | 7/1998 | Cope et al. |
| 5,788,647 | A | 8/1998 | Eggers |
| 5,837,003 | A | 11/1998 | Ginsburg |
| 5,862,675 | A | 1/1999 | Scaringe et al. |
| 5,879,329 | A | 3/1999 | Ginsburg |
| 5,895,418 | A | 4/1999 | Saringer |
| 5,908,407 | A | 6/1999 | Frazee et al. |
| 5,957,963 | A | 9/1999 | Dobak, III |
| 5,980,561 | A | 11/1999 | Kolen et al. |
| 5,989,238 | A | 11/1999 | Ginsburg |
| 6,019,783 | A | 2/2000 | Philips et al. |
| 6,042,559 | A | 3/2000 | Dobak, III |
| 6,042,599 | A | 3/2000 | Huttner |
| 6,051,019 | A | 4/2000 | Dobak, III |
| 6,059,825 | A | 5/2000 | Hobbs et al. |
| 6,096,068 | A | 8/2000 | Dobak, III et al. |
| 6,110,139 | A | 8/2000 | Loubser |
| 6,110,168 | A | 8/2000 | Ginsburg |
| 6,117,065 | A | 9/2000 | Hastings et al. |
| 6,117,105 | A | 9/2000 | Bresnaham et al. |
| 6,124,452 | A | 9/2000 | Di Magno |
| 6,126,684 | A | 10/2000 | Gobin et al. |
| 6,146,141 | A | 11/2000 | Schumann |
| 6,146,411 | A | 11/2000 | Noda et al. |
| 6,148,634 | A | 11/2000 | Sherwood |
| 6,149,624 | A | 11/2000 | Mcshane |
| 6,149,670 | A | 11/2000 | Worthen et al. |
| 6,149,673 | A | 11/2000 | Ginsburg |
| 6,149,676 | A | 11/2000 | Ginsburg |
| 6,149,677 | A | 11/2000 | Dobak, III |
| 6,149,806 | A | 11/2000 | Baer |
| 6,165,207 | A | 12/2000 | Balding |
| 6,188,930 | B1 | 2/2001 | Carson |
| 6,197,045 | B1 | 3/2001 | Carson |
| 6,224,624 | B1 | 5/2001 | Lasheras |
| 6,231,594 | B1 | 5/2001 | Dae |
| 6,231,595 | B1 | 5/2001 | Dobak |
| 6,235,048 | B1 | 5/2001 | Dobak |
| 6,238,428 | B1 | 5/2001 | Werneth |
| 6,245,095 | B1 | 6/2001 | Dobak |
| 6,251,129 | B1 | 6/2001 | Dobak |
| 6,251,130 | B1 | 6/2001 | Dobak |
| 6,254,626 | B1 | 7/2001 | Dobak |
| 6,261,312 | B1 | 7/2001 | Dobak |
| 6,264,679 | B1 | 7/2001 | Keller |
| 6,283,940 | B1 | 9/2001 | Mulholland |
| 6,287,326 | B1 | 9/2001 | Pecor |
| 6,290,717 | B1 | 9/2001 | Philips |
| 6,299,599 | B1 | 10/2001 | Pham et al. |
| 6,306,161 | B1 | 10/2001 | Ginsburg |
| 6,312,452 | B1 * | 11/2001 | Dobak, III ............ A61B 18/02 606/21 |
| 6,325,818 | B1 | 12/2001 | Werneth |
| 6,338,727 | B1 | 1/2002 | Noda et al. |
| 6,365,899 | B1 | 4/2002 | Arai |
| 6,368,304 | B1 | 4/2002 | Aliberto |
| 6,375,674 | B1 | 4/2002 | Carson |
| 6,379,378 | B1 | 4/2002 | Werneth |
| 6,383,144 | B1 * | 5/2002 | Mooney ............... A61B 1/012 600/435 |
| 6,383,210 | B1 | 5/2002 | Magers |
| 6,393,320 | B2 | 5/2002 | Worthen |
| 6,405,080 | B1 | 6/2002 | Lasersohn |
| 6,409,747 | B1 | 6/2002 | Gobin et al. |
| 6,416,533 | B1 | 7/2002 | Gobin et al. |
| 6,419,643 | B1 | 7/2002 | Shimada |
| 6,428,563 | B1 | 8/2002 | Keller |
| 6,450,990 | B1 | 9/2002 | Walker et al. |
| 6,461,379 | B1 | 10/2002 | Carson |
| 6,464,666 | B1 | 10/2002 | Augustine et al. |
| 6,464,716 | B1 | 10/2002 | Dobak, III et al. |
| 6,527,798 | B2 | 3/2003 | Ginsburg et al. |
| 6,530,946 | B1 | 3/2003 | Noda et al. |

(56) References Cited

U.S. PATENT DOCUMENTS

| | | |
|---|---|---|
| 6,544,282 B1 | 4/2003 | Dae et al. |
| 6,551,309 B1 | 4/2003 | Le Pivert |
| 6,554,791 B1 | 4/2003 | Cartledge et al. |
| 6,605,106 B2 | 8/2003 | Schwartz |
| 6,610,083 B2 | 8/2003 | Keller et al. |
| 6,620,187 B2 | 9/2003 | Gruszecki |
| 6,620,188 B1 | 9/2003 | Ginsburg et al. |
| 6,624,679 B2 | 9/2003 | Tomaiuolo et al. |
| 6,635,079 B2 | 10/2003 | Ginsburg |
| 6,645,232 B2 | 11/2003 | Carson |
| 6,660,027 B2 | 12/2003 | Ellingboe |
| 6,669,715 B2 | 12/2003 | Carson |
| 6,673,098 B1 | 1/2004 | Machold et al. |
| 6,679,906 B2 | 1/2004 | Hammack et al. |
| 6,685,733 B1 | 2/2004 | Dae et al. |
| 6,692,518 B2 | 2/2004 | Carson |
| 6,706,060 B2 | 3/2004 | Tzeng et al. |
| 6,716,188 B2 | 4/2004 | Noda et al. |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak, III |
| 6,743,201 B1 | 6/2004 | Donig et al. |
| 6,764,391 B1 | 7/2004 | Grant |
| 6,799,063 B2 | 9/2004 | Carson |
| 6,799,342 B1 | 10/2004 | Jarmon |
| 6,802,855 B2 | 10/2004 | Hoglund |
| 6,818,012 B2 | 11/2004 | Ellingboe |
| 6,827,728 B2 | 12/2004 | Hoglund |
| 6,843,800 B1 | 1/2005 | Dobak, III |
| 6,878,156 B1 | 4/2005 | Noda |
| 6,887,263 B2 | 5/2005 | Bleam et al. |
| 6,893,419 B2 | 5/2005 | Noda et al. |
| 6,969,399 B2 | 11/2005 | Schock et al. |
| 7,070,612 B1 | 7/2006 | Collins et al. |
| 7,510,569 B2 | 3/2009 | Dae et al. |
| 7,666,215 B2 | 2/2010 | Callister et al. |
| 7,822,485 B2 | 10/2010 | Collins |
| 7,846,193 B2 | 12/2010 | Dae et al. |
| 7,857,781 B2 | 12/2010 | Noda et al. |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,226,605 B2 | 7/2012 | Faries et al. |
| 8,272,857 B2 | 9/2012 | Norman et al. |
| 8,888,729 B2 | 11/2014 | Jones |
| 2001/0031946 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0101326 A1* | 8/2002 | Lavenuta ............... G01K 7/226 338/22 R |
| 2002/0145525 A1 | 10/2002 | Friedman et al. |
| 2002/0164169 A1* | 11/2002 | Arai ................... G03G 21/1889 399/12 |
| 2002/0183692 A1 | 12/2002 | Callister |
| 2002/0198579 A1 | 12/2002 | Khanna |
| 2003/0014094 A1* | 1/2003 | Hammack ................ A61F 7/12 607/105 |
| 2003/0036496 A1 | 2/2003 | Elsner et al. |
| 2003/0060863 A1* | 3/2003 | Dobak, III .............. A61F 7/12 607/104 |
| 2003/0088299 A1* | 5/2003 | Magers ................... A61F 7/12 607/104 |
| 2004/0089058 A1 | 5/2004 | De Hann et al. |
| 2004/0102825 A1 | 5/2004 | Daoud |
| 2004/0104018 A1 | 6/2004 | Hughes et al. |
| 2004/0143311 A1 | 7/2004 | Machold et al. |
| 2004/0167467 A1* | 8/2004 | Harrison ................. A61F 7/12 604/113 |
| 2004/0199230 A1* | 10/2004 | Yon ........................ A61F 7/12 607/106 |
| 2004/0210231 A1 | 10/2004 | Boucher et al. |
| 2004/0220647 A1 | 11/2004 | Noda |
| 2004/0267339 A1* | 12/2004 | Yon ............................ A61F 7/12 607/105 |
| 2005/0107741 A1 | 5/2005 | Willard et al. |
| 2005/0156744 A1 | 7/2005 | Pires |
| 2006/0064146 A1 | 3/2006 | Collins |
| 2006/0069418 A1 | 3/2006 | Schock et al. |
| 2006/0122673 A1* | 6/2006 | Callister .................... A61F 7/12 607/105 |
| 2006/0293734 A1 | 12/2006 | Scott et al. |
| 2007/0007640 A1 | 1/2007 | Harnden et al. |
| 2007/0043409 A1* | 2/2007 | Brian, III .................. A61F 7/12 607/105 |
| 2007/0076401 A1 | 4/2007 | Carrez et al. |
| 2008/0009578 A1* | 1/2008 | Khatua .................... C08K 3/22 524/431 |
| 2008/0058792 A1* | 3/2008 | Falkenstein ............ A61B 18/16 606/32 |
| 2008/0230530 A1 | 9/2008 | Augustine et al. |
| 2008/0262409 A1 | 10/2008 | Derrico et al. |
| 2009/0140369 A1* | 6/2009 | Lee ....................... H01L 23/3107 257/467 |
| 2009/0247963 A1 | 10/2009 | Bleam et al. |
| 2009/0299287 A1 | 12/2009 | Carson et al. |
| 2010/0129248 A1 | 5/2010 | Mou |
| 2010/0203367 A1* | 8/2010 | Che ....................... H01M 2/0413 429/61 |
| 2010/0318075 A1* | 12/2010 | Joye .................... A61B 1/00082 606/21 |
| 2011/0022136 A1 | 1/2011 | Scott et al. |
| 2011/0046551 A1 | 2/2011 | Augustine et al. |
| 2011/0137249 A1 | 6/2011 | Collins et al. |
| 2011/0184253 A1 | 7/2011 | Archer et al. |
| 2011/0201956 A1* | 8/2011 | Alferness ................ A61B 1/267 600/532 |
| 2011/0208278 A1 | 8/2011 | Machold et al. |
| 2012/0078247 A1* | 3/2012 | Worrell .............. A61B 18/1445 606/45 |
| 2012/0158103 A1 | 6/2012 | Bledsoe |
| 2013/0079855 A1 | 3/2013 | Helkowski |
| 2013/0079856 A1 | 3/2013 | Dabrowiak |
| 2013/0079858 A1* | 3/2013 | Helkowski ................ A61F 7/12 607/106 |
| 2013/0178923 A1 | 7/2013 | Suzuki |
| 2013/0190744 A1* | 7/2013 | Avram ....................... A61F 7/10 606/21 |
| 2013/0331774 A1 | 12/2013 | Farrell et al. |
| 2013/0333675 A1* | 12/2013 | Seaton ..................... G01K 1/10 123/568.12 |
| 2014/0081202 A1 | 3/2014 | Tsoukalis |
| 2014/0094880 A1 | 4/2014 | Lim |
| 2014/0094881 A1 | 4/2014 | Dabrowiak et al. |
| 2014/0094882 A1 | 4/2014 | Lim |
| 2014/0094883 A1 | 4/2014 | Lim |
| 2014/0113828 A1* | 4/2014 | Gilbert .................. H01L 39/126 505/100 |
| 2014/0276720 A1* | 9/2014 | Parihar ............ A61B 17/07207 606/33 |
| 2015/0101316 A1* | 4/2015 | Seaton ..................... F01N 3/208 60/295 |
| 2015/0105659 A1* | 4/2015 | Salahieh ............ A61B 18/1492 600/435 |
| 2015/0297292 A1* | 10/2015 | Sutermeister ........ A61B 18/082 606/41 |
| 2015/0366608 A1* | 12/2015 | Weber ................ A61B 18/1492 606/41 |
| 2016/0015289 A1* | 1/2016 | Simon ..................... A61B 5/04842 600/301 |

FOREIGN PATENT DOCUMENTS

| | | |
|---|---|---|
| EP | 0951244 B1 | 3/2004 |
| GB | 2040169 | 8/1980 |
| GB | 1163185 | 2/1985 |
| GB | 2212262 | 7/1989 |
| GB | 2383828 | 7/2003 |
| JP | 09-215754 | 8/1997 |

(56) References Cited

FOREIGN PATENT DOCUMENTS

| | | |
|---|---|---|
| JP | 10-0127777 | 5/1998 |
| JP | 10-305103 | 11/1998 |
| JP | 2005-506118 | 3/2005 |
| JP | 2005-131421 | 5/2005 |
| WO | 1990001682 | 2/1990 |
| WO | 1993004727 | 3/1993 |
| WO | 1994000177 | 1/1994 |
| WO | 1994001177 | 1/1994 |
| WO | 95-03680 | 2/1995 |
| WO | 1997025011 | 7/1997 |
| WO | 1998024491 | 6/1998 |
| WO | 1998040017 | 9/1998 |
| WO | 2000010494 | 3/2000 |
| WO | 2001013809 | 3/2001 |
| WO | 0126719 | 4/2001 |
| WO | 2001064148 | 9/2001 |
| WO | 2001076517 | 10/2001 |
| WO | 2001083001 | 11/2001 |
| WO | 2012-0175089 | 12/2012 |

OTHER PUBLICATIONS

F.W. Behmann, E. Bontke, "Die Regelung der Wärmebildung bei künstlicher Hypothermie". Pflügers Archiv. Bd. 266, S. 408-421 (1958).

F.W. Behmann, E. Bontke, "Intravasaie Kühlung ", Pflügers Archiv. Bd. 263, S. 145-165 (1958).

Wilhelm Behringer, Stephan Prueckner, Rainer Kenter, Samuel A. Tisherman, Ann Radovsky, Robert Clark, S. William Stezoski, Heremy Henchir, Edwin Klein, Peter Safar, "Rapid Hypothermic Aortic Flush Can Achieve Survival without Brain Damage after 30 Minutes Cardiac Arrest in Dogs", anesthesiology, V. 93, No. 6, Dec. 2000.

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

Jeremy Thomas Dabrowiak, "Heat Exchange System for Patient Temperature Control with Multiple Coolant Chambers for Multiple Heat Exchange Modalities", related pending U.S. Appl. No. 14/175,545 applicant response to non-final office action filed May 2, 2016.

Jeremy Thomas Dabrowiak, Christoph Matthias Pistor, Craig Wendell Pendry, Christo Pamichev, "Fluid Cassette with Tensioned Polymeric Membranes for Patient Heat Exchange System", related pending U.S. Appl. No. 14/180,613, non-final office action dated May 19, 2016.

Jeremy Thomas Dabrowiak, Christoph Matthias Pistor, Craig Wendell Pendry, Christo Pamichev, "Fluid Cassette with Tensioned Polymeric Membranes for Patient Heat Exchange System", related pending U.S. Appl. No. 14/180,613, applicant's response to non-final office action filed Jun. 1, 2016.

Christoph Matthias Pistor, Jeremy Thomas Dabrowiak, Craig Wendell Pendry, Christo Pamichev, "Fluid Cassette with Polymeric Membranes and Integral Inlet and Outlet Tubes for Patient Heat Exchange System", related pending U.S. Appl. No. 14/180,655, non-final office action dated May 18, 2016.

Christoph Matthias Pistor, Jeremy Thomas Dabrowiak, Craig Wendell Pendry, Christo Pamichev, "Fluid Cassette with Polymeric Membranes and Integral Inlet and Outlet Tubes for Patient Heat Exchange System", related pending U.S. Appl. No. 14/180,655, applicant's response to non-final office action file Jun. 1, 2016.

Jeremy Thomas Dabrowiak, Eric Peterson, "Patient Heat Exchange System with Transparent Wall for Viewing Circulating Refrigerant", related pending U.S. Appl. No. 14/276,202, non-final office action dated May 19, 2016.

Jeremy Thomas Dabrowiak, Eric Peterson, "Patient Heat Exchange System with Transparent Wall for Viewing Circulating Refrigerant", related pending U.S. Appl. No. 14/276,202, applicant's response to non-final office action filed Jun. 1, 2016.

James Mazzone, "Proximal Mounting of Temperature Sensor in Intravascular Temperature Management Catheter", Notification of Transmittal of the International Search Report and the Written Opinion of the International Searching Authority dated Jul. 7, 2016.

Christoph Matthias Pistor, Jeremy Thomas Dabrowiak, Craig Wendell Pendry, Christo Pamichev, "Fluid Cassette with Polymeric Membranes and Integral Inlet and Outlet Tubes for Patient Heat Exchange System", file history of related U.S. Appl. No. 14/180,655, filed Feb. 14, 2014.

Jeremy Thomas Dabrowiak, "Heat Exchange System for Patient Temperature Control with Multiple Coolant Chambers for Multiple Heat Exchange Modalities", file history of related U.S. Appl. No. 14/175,545 filed Feb. 7, 2014.

Jeremy Thomas Dabrowiak, Eric Peterson, "Patient Heat Exchange System with Transparent Wall for Viewing Circulating Refrigerant", file history of related U.S. Appl. No. 14/276,202, filed May 13, 2014.

Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump" file history of related U.S. Appl. No. 14/534,718, filed Nov. 6, 2014.

Jeremy Thomas Dabrowiak, Christoph Matthias Pistor, Craig Wendell Pendry, Christo Pamichev, "Fluid Cassette with Tensioned Polymeric Membranes for Patient Heat Exchange System", file history of related U.S. Appl. No. 14/180,613, filed Feb. 14, 2014.

Jeremy Thomas Dabrowiak, Mark Davey. "Serpentine Heat Exchange Assembly for Removable Engagement with Patient Heat Exchange System", file history of related U.S. Appl. No. 14/675,421, filed Mar. 31, 2015.

Jeremy Thomas Dabrowiak, Craig Wendell Pendry, Christoph Matthias Pistor, "Cold Plate Design in Heat Exchanger for Intravascular Temperature Management Catheter and/or Heat Exchange Pad", file history of related U.S. Appl. No. 14/675,504, filed Mar. 31, 2015.

Christo Petrov Pamichev, Jeremy Thomas Dabrowiak, "Working Fluid Cassette with Hinged Plenum or Enclosure for Interfacing Heat Exchanger with Intravascular Temperature Management Catheter", file history of related U.S. Appl. No. 14/676,672, filed Apr. 1, 2015.

Christo Petrov Pamichev, Jeremy Thomas Dabrowiak, "Heat Exchange System or Patient Temperature Control With Easy Loading High Performance Peristaltic Pump", file history of related U.S. Appl. No. 14/676,682, filed Apr. 1, 2015.

Jeremy Thomas Dabrowiak, Craig Wendell Pendry, Christoph Matthias Pistor, "Patient Heat Exchange System with Two and Only Two Fluid Loops", related U.S. Appl. No. 14/180,719, Non-Final Office Action dated Jun. 7, 2016.

Supplementary European Search Report from the counterpart EP application No. 16774074.01, dated Oct. 24, 2018.

\* cited by examiner

PROXIMAL MOUNTING OF TEMPERATURE SENSOR IN INTRAVASCULAR TEMPERATURE MANAGEMENT CATHETER

TECHNICAL FIELD

The present application relates generally to heat exchange systems for patient temperature control with proximally mounted joining bodies or ceramic portions of an onboard temperature sensor.

BACKGROUND

Patient temperature control systems have been introduced to prevent fever in patients in the neuro ICU due to suffering from sub-arachnoid hemorrhage or other neurologic malady such as stroke. Also, such systems have been used to induce mild or moderate hypothermia to improve the outcomes of patients suffering from such maladies as stroke, cardiac arrest, myocardial infarction, traumatic brain injury, and high, intracranial pressure. Moreover, such systems have been used for warming purposes such as for burn patients and other patients who may suffer from deleterious or accidental hypothermia. Examples of intravascular heat exchange catheters are disclosed in U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559, 8,888,729, and U.S. Provisional Patents 2013/0178923, 2013/0079855, 2013/0079856, 2014/0094880, 2014/0094882, 2014/0094883, all of which are incorporated herein by reference.

External patient temperature control systems may be used. Such systems are disclosed in U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference.

One or more of the above-referenced catheters may be equipped with a temperature sensor on the catheter to sense the temperature of blood flowing past the catheter. The temperature signal is fed back to the controller of one or more of the above-referenced systems and used to control the temperature of the working fluid circulating through the catheter.

SUMMARY

As understood herein, the desirability of minimizing the diameter of the catheter limits space on the intubated portion of the catheter that is available to support a temperature sensor. Accordingly, an intravascular temperature management catheter includes a catheter shaft through which working fluid can circulate to and from a proximal location on the shaft. The catheter extends from a connector hub. At least one heat exchange member is supported by a part of the shaft, e.g., a distal part of the shaft, or by a catheter spine or other catheter portion, to receive circulating working fluid from the proximal location. One or more temperature sensors are supported on or in the catheter for generating a temperature signal representative of blood temperature to a control system. The temperature sensor includes first and second conductive leads having respective first and second distal segments on or in the catheter shaft. The first and second distal segments are arranged to be in thermal contact with blood flowing past the catheter when the catheter is disposed in a blood vessel of a patient. Also, the temperature sensor includes a joining body connected to proximal segments of the first and second leads, wherein the temperature sensor is positioned or oriented such that the joining body is in a location which is proximal to the first and second conductive leads, e.g., the joining body maybe supported on or in the hub, an electrical connector or in another location proximal to the hub.

In examples, the temperature sensor may be a thermistor or other type of temperature sensor or detector, including but not limited to thermocouples, resistance temperature detectors (RTDs), or fiber optic temperature sensors. The temperature sensor can be a negative temperature coefficient (NTC) thermistor or a positive temperature coefficient (PTC) thermistor. The joining body may be made of various materials, e.g., a polymer or a ceramic. For instance the joining body can be made of sintered metal oxide. Or, the joining body, without limitation, may be made of a doped polycrystalline ceramic. If desired, a thermally conductive cover can physically shield the first and second distal segments from contact with blood flowing past the catheter when the catheter is disposed in a blood vessel of a patient.

In another aspect, a method includes thermally exposing first and second distal segments of first and second leads of one or more temperature sensors mounted on or in a closed loop intravascular temperature management catheter to blood flowing past the catheter. The method includes receiving a signal representing blood temperature from a joining body, e.g., a ceramic or polymer joining body, connected to the leads, wherein the temperature sensor is positioned or oriented such that the joining body is disposed in a location which is proximal to at least a portion of the first and second conductive leads or distal segments of the leads and/or disposed on or in a proximal hub of the catheter, an electrical connector, or in a location proximal to the hub, and sending the signal to a control system for controlling a temperature of working fluid flowing through the catheter in a closed loop.

In another aspect, a device has a catheter shaft through which working fluid can circulate and one or more temperature sensors supported on or in the device for generating a temperature signal. The temperature sensor includes first and second conductive leads having respective first and second distal segments arranged to be in thermal contact with blood flowing past the catheter when the catheter is disposed in a blood vessel of a patient. Also, the temperature sensor has a joining body connected to proximal segments of the first and second leads, with the joining body being supported in a location proximal to the distal segments of the first and second leads. The temperature sensor may be positioned or oriented such that the joining body is in a location which is proximal to at least a portion of the distal segments of the first and second conductive leads, e.g., supported on or in the hub, an electrical connector, or in location proximal to a hub.

The details of the various embodiments and aspects described herein, both as to their structure and operation, can best be understood in reference to the accompanying drawings, in which like reference numerals refer to like parts, and in which:

BRIEF DESCRIPTION OF THE PEA WINGS

DETAILED DESCRIPTION

Figure 1:
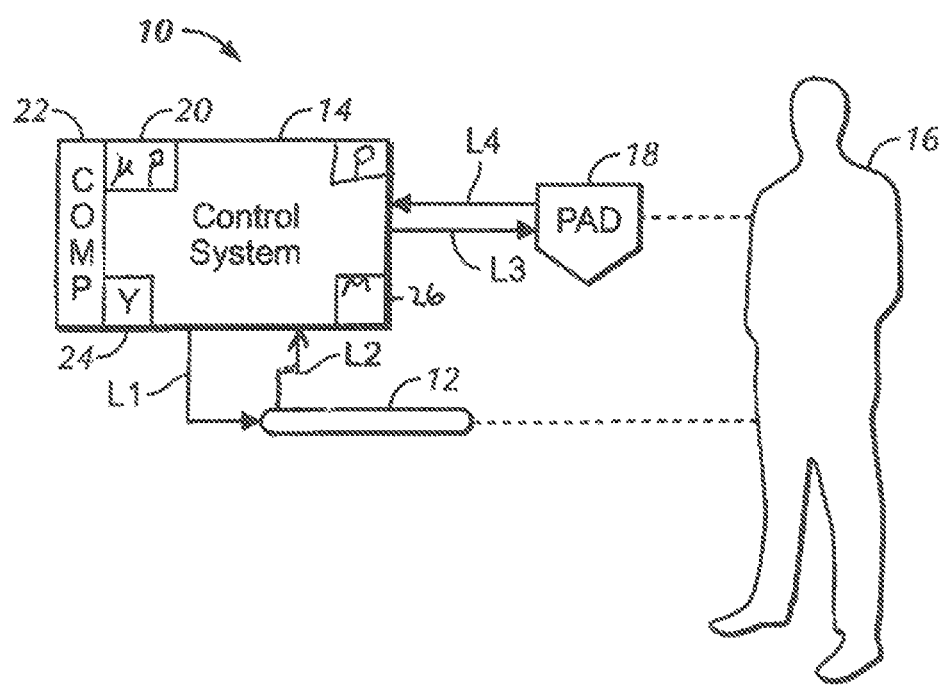
FIG. 1 is a schematic view of a non-limiting system in accordance with an embodiment of the present invention.

Referring initially to FIG. 1, in accordance with present principles, a system 10 may include one or more intravascular heat exchange catheters 12 controlled by a control system 14 to control patient temperature, e.g., to prevent the patient 16 from becoming febrile or to induce therapeutic hypothermia in the patient 16. In the catheter, working fluid or coolant, such as but not limited to saline, circulates (typically under the influence of a pump "P" in the control system) in a closed loop from the control system 14, through a fluid supply line L1, through the catheter 12, and back to the system 14 through a fluid return line L2, such that no working fluid or coolant enters the body. In this way, patient temperature can be managed by controlling the temperature of the working fluid as appropriate to exchange heat with the blood. Without limitation, the catheter 12 may be implemented by any of the catheters disclosed in the patent documents incorporated by reference herein in the following U.S. patent documents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,323,818, 6,409,747, 6,368,304, 6,338,727, 6,299,599, 6,287,326, 6,126,684, 8,888,729, and U.S. Provisional Patents 2013/0178923, 2013/0079855, 2013/0079856, 2014/0094880, 2014/0094882, 2014/0094883. The catheter 12 maybe placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by the control system 14 to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady the effects of which can be ameliorated by hypothermia. The pad 18 may receive working fluid from the system 14 through a fluid supply line L3, and return working fluid to the system 14 through a fluid return line L4.

The control system 14 may include one or more microprocessors 20 receiving target and patient temperatures as input and controlling, among other things, the pump "P" and a refrigerant compressor 22 and/or a bypass valve 24 that can be opened to permit refrigerant to bypass a condenser. The refrigerant circulates through a heat exchanger within the control system 14 as described further below. The processor 20 can access non-transitory computer memory 26 to execute instructions on the memory 26 to execute control logic.

Figure 2:
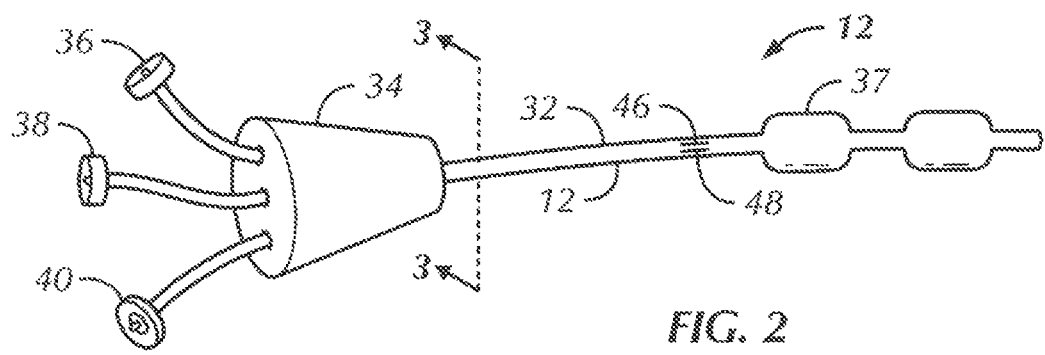
FIG. 2 is a perspective view of an example catheter.
Figure 3:
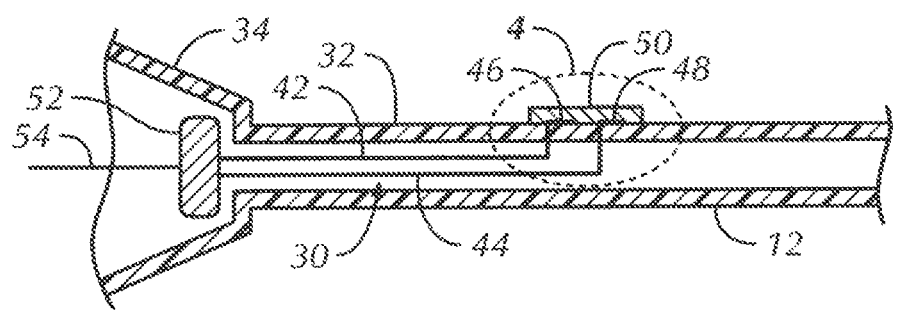
FIG. 3 is a cross-section taken along the line 3-3 in FIG. 2.
Figure 4:
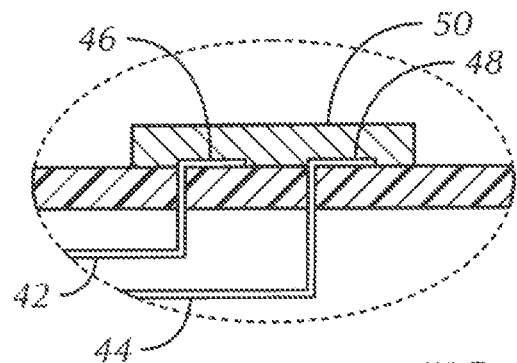
FIG. 4 is a close up view of the top portion of the structure shown in circle 4 in FIG. 3.

As shown in the embodiment in FIGS. 2-4, a temperature sensor 30, e.g., a thermistor, may be supported on the catheter 12. As shown, the catheter 12 may have one or more hollow multi-lumen shaft portions 32 (a catheter with only a single shaft shown) through which working fluid can circulate to and from a proximal location on the shaft, at which the catheter shaft extends from a connector hub 34.

The connector hub 34 fluidly interconnects working fluid supply and return lumens in the catheter shall 32 to respective supply and return connector fittings 36, 38, which may be connected via respective tubing set connectors to the system 34 shown in FIG. 1 in which the working fluid may be heated or cooled as desired to manage patient temperature.

The working fluid circulating in the supply and return lumens of the shaft 32 circulate into and out of one or more heat exchange members 37 that are supported by a distal part of the shaft 32 or by another part of the catheter. Any of the heat exchange members described in the patents may be used.

Additionally, a temperature connector 40 may provide electrical communication between the temperature sensor 30 and the system 14. One or more electrical connectors may extend from the temperature sensor 30 through the temperature connector 40, which may be engaged with a corresponding connector engaged with the system 14 to provide a path tor electrical signal transmission from the temperature sensor 30 to the system 14. Alternatively, a wireless transceiver may be provided, e.g., in the hub 34 to receive the temperature signal from the temperature sensor 30 and wirelessly transmit the signal to the system 14. While three connectors 36-40 are shown, it is to be understood that additional connectors may be provided on the hub 34. For example, a medicament infusion connector may be provided that fluidly connects an infusion lumen in the catheter shaft 32 with a source of medicament.

FIGS. 3 and 4 best show that the temperature sensor 30 includes at least first and second conductive leads 42, 44 having respective first and second distal segments 46, 48 (also shown schematically in FIG. 2) on or in the catheter shaft 32. The leads 42, 44 may be molded into the wall of the catheter shaft 32 and extend proximally to the hub 34, or the leads 42, 44, with the possible exception of the distal segments 46, 48, may be disposed in a lumen of the catheter shaft 32.

In examples, the first and second distal segments 46, 48 are arranged to be in thermal contact with blood flowing past the catheter when the catheter is disposed in a blood vessel of a patient. In the example shown, the distal segments 46, 48 lie on the catheter shaft parallel to the axis of the shaft and on or near the outer surface of the shaft. In some embodiments the distal segments 46, 48 may be molded into the shaft and may lie on the outer surface, physically and thus thermally exposed to blood flowing past the catheter. In other embodiments the distal segments 46, 48 may be covered by a thermally conductive cover 50 to physically shield the distal segments 46, 48 from blood while thermally coupling the segments to the blood. In an example, the cover 50 may be established by an ultra-thin and flexible metal foil that can be wrapped around the catheter shaft 32. Other materials may be used, e.g., thermally conductive plastic. In certain embodiments, a temperature sensor may have one or more leads.

As mentioned above, the first and second conductive leads 42, 44 may extend to and if desired into the hub 34, where proximal segments of the leads are connected to a joining body 52 or body (FIG. 3) which may be supported in the hub or in a location proximal to the hub, e.g., in or on a connector, such as an electrical or temperature connector. It is to be understood that electrical signals representing patient temperature are taken from the joining body 52 and sent (e.g., via a lead 54 and the temperature connector 40) to the system 14 according to principles described above. The temperature sensor may be positioned or oriented such that the joining body is in a location proximal to or proximal relative to the position of at least a portion of the first and/or second conductive leads, e.g., the distal segment of a lead, whether the joining body is positioned on or in the catheter, hub or other location proximal to the hub. In certain embodiments, a joining body may be located proximal to or proximal relative to at least a portion of the first and second conductive leads such that it is closer to a proximal end of the catheter, a hub or other connector than the location of at least a portion of the conductive leads is.

In any of the embodiments described herein, the temperature sensor 30 may be a thermistor or other type of sensor or detector, including but not limited to thermocouples, resistance temperature detectors (RTDs), or fiber optic temperature sensors. For example, a thermistor can be a negative temperature coefficient (NTC) or positive temperature coefficient (PTC) thermistor. The thermistor may include the first and second electrically conductive leads or wires 42, 44 which may be electrically insulated within the catheter and which join the joining body 52, which may fee a ceramic or polymer body. For example, NTC thermistors may have joining bodies made from a pressed disc, rod, plate, bead or cast chip of a semiconductor such as a sintered metal oxide, whereas a PTC thermistor may have a joining body made of a polycrystalline ceramic doped with barium titanate (Ba-TiO3).

While various embodiments of a PROXIMAL MOUNTING OF TEMPERATURE SENSOR IN INTRAVASCULAR TEMPERATURE MANAGEMENT CATHETERS are herein shown and described in detail, the scope of the present invention is to be limited by nothing other than the appended claims.

What is claimed is:

1. An intravascular temperature management catheter, comprising:
   at least one catheter shaft through which working fluid can circulate to and from a proximal location on the at least one catheter shaft, the catheter shaft extending from a hub;
   at least one heat exchange member configured to receive circulating working fluid from the proximal location; and
   at least one temperature sensor supported on or in the catheter shaft for generating a temperature signal representative of blood temperature to a control system, the temperature sensor comprising:
      at least first and second conductive leads having respective first and second distal segments supported by a distal portion of the catheter shaft and extending to an outer surface of the catheter shaft without increasing a diameter of the catheter shaft, the first and second distal segments being coupled to the catheter shaft so that the first and second distal segments are parallel to an axis of the catheter shaft and parallel to each other at a fixed distance apart, with blood flowing past the catheter shaft and directly across the first and second distal segments when the catheter shaft is disposed in a blood vessel of a patient, the temperature sensor further comprising a joining body connected to proximal segments of the first and second conductive leads, wherein the joining body is supported in or on the hub or in a location proximal to the hub.

2. The intravascular temperature management catheter of claim 1, whrein the at least one temperature sensor is a thermistor.

3. The intravascular temperature management catheter of claim 2, wherein the thermistor is a negative temperature coefficient (NTC) thermistor.

4. The intravascular temperature management catheter of claim 2, wherein the thermistor is a positive temperature coefficient (PTC) thermistor.

5. The intravascular temperature management catheter of claim 1, wherein the joining body is made of a polymer.

6. The intravascular temperature management catheter of claim 1, wherein the joining body is made of a ceramic.

7. The intravascular temperature management catheter of claim 1, wherein the joining body is made of sintered metal oxide.

8. The intravascular temperature management catheter of claim 1, whrein the joining body is made of a doped polycrystalline ceramic.

9. The intravascular temperature management catheter of claim 1, further comprising a thermally conductive cover to physically shield at least portions of the respective first and segment distal segments from contact with blood flowing past the catheter shaft when the catheter shaft is disposed in a blood vessel of a patient.

10. A method comprising:
   physically exposing a first and second distal segments of first and second leads of a temperature sensor, the first and second distal segments being embedded in an outer surface of a closed loop intravascular temperature management catheter and supported by a distal portion of a catheter shaft, the first and second distal segments being parallel to an axis of the catheter shaft and parallel to each other at a fixed distance apart on the outer surface of the catheter shaft, to blood flowing past the catheter shaft, the first and second distal segments extending to an outer surface of the catheter shaft without increasing a diameter of the catheter shaft;
   receiving a signal representing blood temperature from a joining body connected to the first and second leads, wherein the temperature sensor is positioned such that the joining body is disposed in a location which is proximal to at least a portion of the first and second leads; and
   sending the signal to a control system for controlling a temperature of working fluid flowing through the catheter shaft in a closed loop.

11. The method of claim 10, wherein the catheter shaft extends from a connector hub and the joining body is disposed on or in the connector hub or in a lcoation proximal to the connector hub.

12. A device comprising:
   a catheter shaft through which working fluid can circulate; and
   at least one temperature sensor supported on or in the device for generating a temperature signal, the temperature sensor comprising:
      at least first and second conductive leads having respective first and second distal segments supported by a distal portion of the catheter shaft, the first and second distal segments being arranged to be in contact with blood flowing past the catheter shaft and directly across the first and second distal segments when the catheter shaft is disposed in a blood vessel of a patient and extending to an outer surface of the catheter shaft without increasing a diameter of the catheter shaft, the first and second distal segments being coupled to the catheter shaft so that the first and second distal segments are parallel to an axis of the catheter shaft and parallel to each other at a fixed distance apart.

13. The device of claim 12, wherein the catheter shaft extends from a hub and a joining body is disposed on or in the hub or in a location proximal to the hub.

14. The device of claim 13, wherein the joining body is made of a polymer.

15. The device of claim 13, wherein the joining body is made of a ceramic.

16. The device of claim 13, wherein the joining body is made of sintered metal oxide.

17. The device of claim 13, wherein the joining body is made of a doped polycrystalline ceramic.

18. The device of claim 12, wherein the at least one temperature sensor is a thermistor.

19. The device of claim 18, wherein the thermistor is a negative temperature coefficient (NTC) thermistor.

20. The device of claim 18, wherein the thermistor is a positive temeprature coefficient (PTC) thermistor.

21. The device of claim 12, further comprising a thermally conductive cover to physically shield at least portions of the respective first and segment distal segments from contact with blood flowing past the catheter shaft when the catheter shaft is disposed in a blood vessel of a patient.

* * * * *

UNITED STATES PATENT AND TRADEMARK OFFICE
CERTIFICATE OF CORRECTION

PATENT NO. : 11,213,423 B2
APPLICATION NO. : 14/675452
DATED : January 4, 2022
INVENTOR(S) : James Mazzone Page 1 of 1

It is certified that error appears in the above-identified patent and that said Letters Patent is hereby corrected as shown below:

On the Title Page

Column 2, Line 4 under "OTHER PUBLICATIONS", after "2016.", insert -- (1156-117). --

In the Claims

Column 5, Line 66, Claim 2, delete "whrein" and insert -- wherein --

Column 6, Line 15, Claim 8, delete "whrein" and insert -- wherein --

Column 6, Line 21, Claim 9, delete "segment" and insert -- second --

Column 6, Line 49, Claim 11, delete "lcoation" and insert -- location --

Column 7, Line 20, Claim 20, delete "temeprature" and insert -- temperature --

Column 7, Line 23, Claim 21, delete "segment" and insert -- second --

Signed and Sealed this
Twenty-sixth Day of July, 2022

Katherine Kelly Vidal
*Director of the United States Patent and Trademark Office*